United States Patent [19]

Bloomfield, III

[11] Patent Number: 4,731,849
[45] Date of Patent: Mar. 15, 1988

[54] ELECTRONIC AUSCULSCOPE

[76] Inventor: John W. Bloomfield, III, P.O. Box 6427, Hilton Head Island, S.C. 29938

[21] Appl. No.: 890,502

[22] Filed: Jul. 30, 1986

[51] Int. Cl.$^4$ .............................................. A61B 7/04
[52] U.S. Cl. ....................................... 381/67; 128/715
[58] Field of Search ........................... 381/67; 128/715

[56] References Cited

U.S. PATENT DOCUMENTS

| | | | |
|---|---|---|---|
| 3,396,241 | 8/1968 | Anderson | 381/67 |
| 3,539,724 | 11/1970 | Keesee | 381/67 |
| 3,651,798 | 3/1972 | Egli | 381/67 |
| 4,226,248 | 10/1980 | Manoli | 381/67 |
| 4,528,690 | 7/1985 | Sedgwick | 128/715 |
| 4,546,777 | 10/1985 | Groch | 128/715 |
| 4,618,986 | 10/1986 | Hower | 128/715 |
| 4,628,939 | 12/1986 | Little | 128/715 |

FOREIGN PATENT DOCUMENTS

| | | | |
|---|---|---|---|
| 1295381 | 5/1962 | France | 381/67 |
| 464105 | 6/1951 | Italy | 381/67 |

*Primary Examiner*—Jin F. Ng
*Assistant Examiner*—L. C. Schroeder
*Attorney, Agent, or Firm*—Fleit, Jacobson, Cohn & Price

[57] ABSTRACT

A battery source of dc voltage continuously energizes digital circuitry for controlling operation of analog signal processing circuitry including a microphone preamplifier, an automatic gain control amplifier, a bandpass section and an output buffer driving audio reproducing equipment. The analog signal processing circuitry is energized on select command from the battery source through a switched on power supply. Automatic operation of the gain control amplifier may be disabled and the bandpass section by-passed in response to other select commands.

27 Claims, 5 Drawing Figures

ELECTRONIC AUSCULSCOPE

BACKGROUND OF THE INVENTION

This invention relates to auscultation or listening to sounds in the chest, abdomen and other parts of the anatomy to enable determination of the condition of the heart, lungs, etc., by physicians, veterinarians and other medical personnel including medical students.

The use of stethoscopes by medical personnel for sound listening diagnosis, if of course, well known. Because of its limitations, the traditional stethoscope does not enable the physician to discriminate between and select sound frequencies of diagnostic value. Further, traditional stethoscopes cannot cope with the wide range of signal amplitudes which call for variable amplification and distortion free audio reproduction. An instrument capable of providing the necessary operational characteristics and functional control for overcoming the limitations of the traditional stethoscope, without sacrifice of its efficiency, has been proposed and is generally referred to as an ausculscope.

It is, therefore, an important object of the present invention to provide a portable ausculscope apparatus for processing sound signals picked up by chest piece microphones, transducers or the like to be reproduced through earphone speakers and other audio reproducing equipment, such apparatus having automatic gain control, frequency bandpass discrimination and amplitude adjustment capabilities to enable frequency selection, sound enhancement and unwanted noise elemination for more accurate and meaningful medical diagnosis purposes.

SUMMARY OF THE INVENTION

In accordance with the present invention, the audio analog signals from the microphone or transducer input of the ausculscope are processed by analog circuitry in a preamplifier and variable gain amplifier through which automatic signal gain control may be exercized. The amplified analog signal is fed either directly to an output buffer or through a bandpass section to the buffer for driving headphone speakers. The bandpass section is selectively by-passed under control of signal commands generated by a switching control section in response to actuation of a bandpass select touch switch, while the automatic gain control operation of the variable gain amplifier may be disabled in favor of fixed gain operation by actuation of an AGC control switch. A second touch switch associated with the switching control section is actuated to cause generation of power select commands which control or regulate operation of the AGC switch, the output buffer section and a power splitting section to which a dc voltage source is connected.

The dc voltage source continuously powers digital circuitry associated with a negative feedback loop controlling automatic gain operation of the variable gain amplifier and an analog signal gate section through which the bandpass section is selectively by-passed in response to the bandpass select commands generated by actuation of one of the touch switches as aforementioned, in accordance with two different modes selected by the user. The analog signal processing circuitry is powered under control of the power select commands aforementioned, at lower voltages, through the switching control section and the power splitting section. A negative voltage from the power splitting section is applied to a ground line for the digital circuitry referenced with respect to zero ground for the analog circuitry.

The negative feedback loop which controls automatic operation of the variable gain amplifier, varies signal gain as an inverse function of input signal amplitude below a preset amplitude limit. Digital gate circuitry disables such automatic operation of the negative feedback loop, in response to actuation of the AGC switch aforementioned, only when power is switched on in response to the power select commands. Power select commands also control grounding circuits in the buffer section for the speakers to avoid reproduction of undesirable noises during power-up and power-down sequences.

The condition of the digital gates controlling bandpass and automatic gain operations is registered through an indicator section turned on in response to power select command.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE PREFERRED EMBODIMENTS

Figure 1:
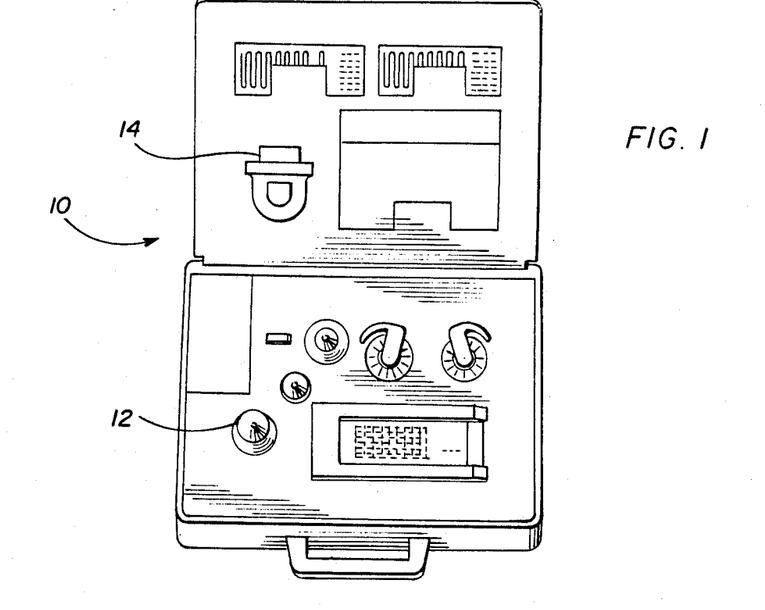
FIG. 1 is a top plan view of a typical ausculscope instrument assembly in a carrying case for use in accordance with the present invention.

Referring now to the drawings in detail, FIG. 1 shows an assembly of components in a carrying case associated with an ausculscope apparatus, generally referred to by reference numeral 10, having an interchangeable vascular chestpiece 12 constituting a transducer or microphone through which input sound signals are picked up. Such input signals are processed in accordance with the present invention by a system schematically depicted in FIG. 2, for audio reproduction by earphone-type speakers 14.

Figure 2:
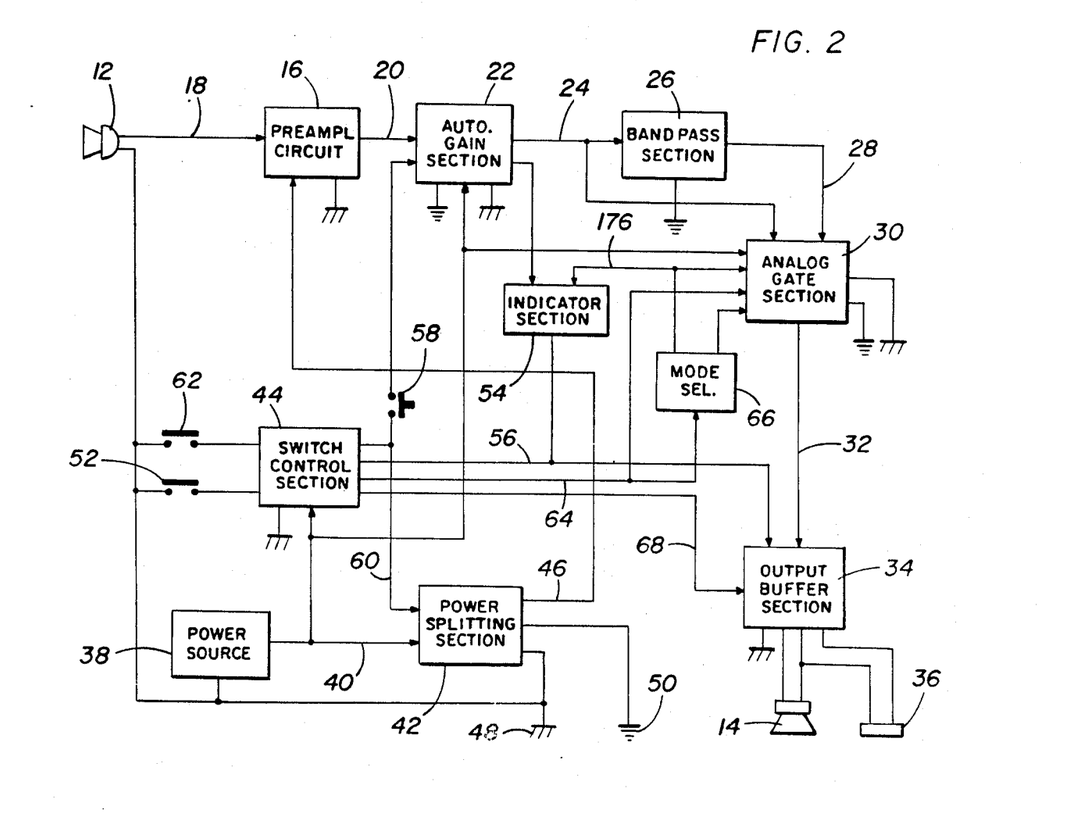
FIG. 2 is a functional block diagram of the signal control and processing system associated with the present invention.

The system schematically depicted by the block diagram of FIG. 2, includes a preamplifier circuit 16 connected to the microphone 12 by input signal line 18. The output of preamplifier 16 is fed by line 20 to an automatic gain control (AGC) section 22. The amplified output of section 22 is transmitted by line 24 by an analog gate section 30 to line 32 either through a bandpass section 26 and line 28, or directly through the gate section 30 from line 24 by-passing the bandpass section 26. The bandpass section 26 when switched in provides for frequency discrimination within a selected one of a plurality of bandpasses. The output signals in line 32 drive the earphone speakers 14 through an output buffer section 34. Stereo phono jack 36 provides for plug in of other equipment through which audio reproduction may be effected.

The ausculscope 10 is powered from a dc power supply 38, also depicted in FIG. 2, from which a relatively high positive dc voltage line 40 extends to the AGC section 22, a power splitting section 42 and a switching control section 44. The power (+9.6 V) in line 40 is split by section 42 between a relatively lower positive dc voltage line 46 (+2.5 V) and a negative dc voltage (−2.5 V) applied to a digital ground 48 referenced with respect to an analog ground 50. The digital ground 48 is connected to the microphone 12, the preamplifier circuit 16, the switching control section 44 and the digital circuitry in the AGC section 22, the analog gate section 30 and the output buffer section 34. The analog ground 50 is connected to the analog circuitry in the AGC section 22, the bandpass section 26 and the output buffer section 34.

The high dc voltage (+9.6 V) in line 40 continuously powers the digital circuitry in the power splitting section 42, the AGC section 22 and in the switching control section 44. The lower dc voltage (+2.5 V) in line 46 powers the analog circuitry in the preamplifier circuit 16 and the digital circuitry through digital ground 48 under control of a power select touch switch 52 connected to the switching control section 44, which also controls the supply of power (at +9.2 VDC) to the output buffer section 34 and an indicator section 54 through voltage line 56. The indicator section 54 registers the operational conditions of AGC section 22 and analog gate section 30.

The operational condition of AGC section 22 is controlled by actuation of AGC select switch 58, except when disabled by the switching control section 44, while the ausculscope power is switched off under command of the power select switch 52 associated with the chestpiece 12 as shown in FIG. 2. The switching control section 44 provides a rapid power-up command in response to actuation of power select switch 52 and a slow power-down command in response to release of the switch 52. The power-up command not only enables AGC select switch 58 but also enables the power splitting section 42 through control line 60.

Actuation of a bandpass select touch switch 62 operates through the switching control section 44 to deliver a command signal through control line 64 to the analog gate section 30 to switch-in the bandpass section 26. A mode selector 66 enables the user to select the operational mode of bandpass selection. In one mode, actuation of switch 62 switches in the bandpass section and upon release the bandpass section is automatically switched out or by-passed. In the other mode, each momentary closing and opening of the select switch 62 will alternately switch in and switch out the bandpass section 26.

Operation of the output buffer section 34 is controlled by the supply of power thereto in line 56 under control of the power commands aforementioned. As a result of such control, the headphones 14 are momentarily disabled during a start-up period in response to a power-up command in order to permit the power supply and the signal processing circuitry to settle before normal operation of the headphones is allowed. Removal of the power supply to the analog circuitry in the output buffer section is delayed in response to a power-down command exercized through control line 68 in order to avoid noise "pops" in the headphones.

Figures 3, 3A:
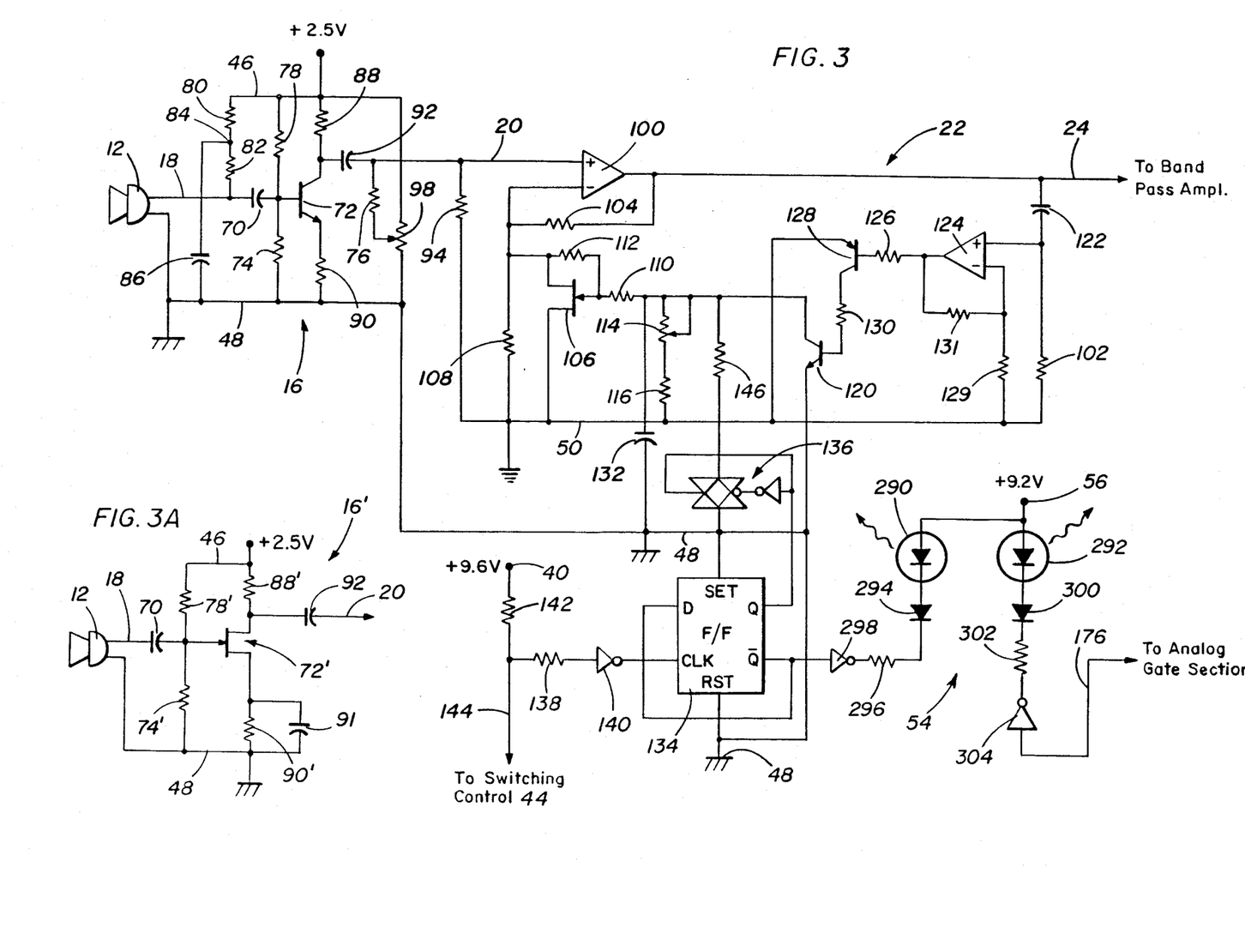
FIGS. 3 through 5 are detailed electrical circuit diagrams forming the system schematically depicted in FIG. 2.

Referring now to FIG. 3, the microphone 12 is coupled by its input signal line 18 and blocking capacitor 70 to the input base of transistor 72 of the preamplifier circuit 16. The transistor base bias is controlled above ground 48 by resistor 74 and at a voltage level below that of voltage supply line 46 by resistor 78. Capacitor 70 and resistors 74 and 78 form a high pass filter. The microphone 12 is effectively decoupled from the voltage supply line 46 by a low pass filter formed by resistors 80 and 82 connected in series between the voltage supply line 46 and the signal line 18 by a junction 84 to which grounded capacitor 86 is connected. Transistor 72 is thereby arranged in a common-emitter amplifier configuration producing an output at its collector at AN AC gain set by the impedance ratio of load resistor 88, interconnected between the voltage supply line and the collector, to the emitter ground leg resistor 90. The audio signals processed by the foregoing preamplifier circuit are coupled by blocking capacitor 92 to the automatic gain control circuit 22 through line 20.

An alternative preamplifier circuit 16' is shown in FIG. 3A, wherein a common source field effect transistor 72' is utilized in an inverting amplifier configuration. In this circuit, bias is established by resistors 74' and 78' for the input gate coupled by capacitor 70 to the audio input signal line 18 from the microphone 12. The FET 72' is set for proper operation by the impedance ratio of resistor 88' to the grounded impedance leg formed by parallel connected resistor 90' and capacitor 91. Capacitor 92 couples the output of FET 72' to the automatic gain control section 22 through line 20.

With continued reference to FIG. 3, line 20 is maintained close above analog ground 50 by resistor 94 and below the base voltage level by fixed resistor 96 and adjustable resistor 98 connected in series therewith. Line 20 is connected to the non-invereting input of an AC variable gain amplifier 100 of the automatic gain control section 22 having its output line 24 coupled by feedback resistor 104 to the inverting input in parallel with a negative feedback loop through which automatic gain control is exercized. The negative feedback loop includes a field effect transistor 106 connected to the inverting input of amplifier 100 and through resistor 108 to ground 50. The apparent impedance of resistor 108 is varied by an input to the gate of transistor 106 in order to correspondingly vary the gain of the output signal in line 24. Circuit distortion is minimized by supply of the input to the gate of transistor 106 through resistor 110 and signal feedback through resistor 112. Offset input voltage to amplifier 100 over the entire operating range of AGC section 22 is compensated for by adjustment of resistor 98 while resistor 114 is adjusted to mid-scale and power is switched off a sufficient length of time (5 seconds) to permit the AGC section 22 to stabilize. Resistor 108 controls the bias level of transistor 106 above ground 50 to which resistor 114 is connected in series with resistor 116.

The negative feedback loop between the output line 24 of the AGC section 22 and the inverting input of amplifier 100 also includes a gain controlling transistor 120 and a capacitor 122 held to a charge level above ground 48 by resistor 102 to allow AGC operation even with some misadjustment of resistor 114. The capacitor 122 couples the output line 24 to the non-inverting input of an amplifier 124 having its output terminal connected by resistor 126 to the base of transistor 128. The inverting input of amplifier 124 is connected to ground 50 through resistor 129 and to the output terminal through a feedback resistor 131. The transistor 128 thereby acts as an audio detector with its emitter connected to ground 50 so that it is turned on when its base is forward biased by a waveform component of the amplified audio signal in line 24 dropping below a lower limit. Transistor 120 having its input base coupled by resistor 130 to the collector of resistor 128, is turned on and off at the same time as transistor 128. Transistor 120 acts as a voltage translator to discharge capacitor 122 toward the level of ground 48 when audio detector transistor 128 is turned on. Capacitor 122 thereby holds the input gate of transistor 106 at a voltage level necessary to provide correct gain determined by the audio detector transistor 128. Resistors 114 and 116 constantly tend to charge a capacitor 132 toward the level of ground 48. While transistors 128 and 120 are turned on, however, capacitor 132 is discharged toward the level of ground 50. A balance between discharge and charge is established within a predetermined range of peak to peak voltage level in line 24. By virtue of such arrangement, a variation in signal amplitude in the output signal line 24 will vary the frequency with which transistors 120 and 128 are turned on and inversely vary the charge of capacitor 132 through resistors 114 and 116. Adjustment of resistor 114 will thereby enable adjustment of the recovery characteristics of the AGC section 22 to satisfy different requirements. Further, if the input signal in line 20 should exceed a predetermined peak voltage limit, automatic gain control function of section 22 is disabled and it then behaves as a simple amplifier with a fixed gain of two, for example.

The AGC section 22 is also disabled through a flip-flop 134 having a Q output connected to signal transmission gate 136. The clock terminal of flip-flop 134 is connected to the dc voltage line 40 through resistors 138 and 142 and inverter 140. One side of gate 136 is connected to ground 48. By closing normally open AGC control switch 58 connected by line 144 to resistor 138, a pulse is generated and applied to the clock terminal of flip-flop 134. As a result, the $\bar{Q}$ output of flip-flop 134 goes high to turn on the gate 136 through inverter 128 while the Q output goes low. When turned on, the gate 136 discharges capacitor 132 to ground 48 through resistor 146 to cut off the transistor 106 and disable the negative feedback loop through which automatic gain control operation is effected. The AGC section 22 will then act as a simple, non-inverting, fixed gain amplifier. The AGC section is returned to normal automatic operation when the control flip-flop 134 is again toggled by switch 58 causing its $\bar{Q}$ output to go low.

Figure 5:
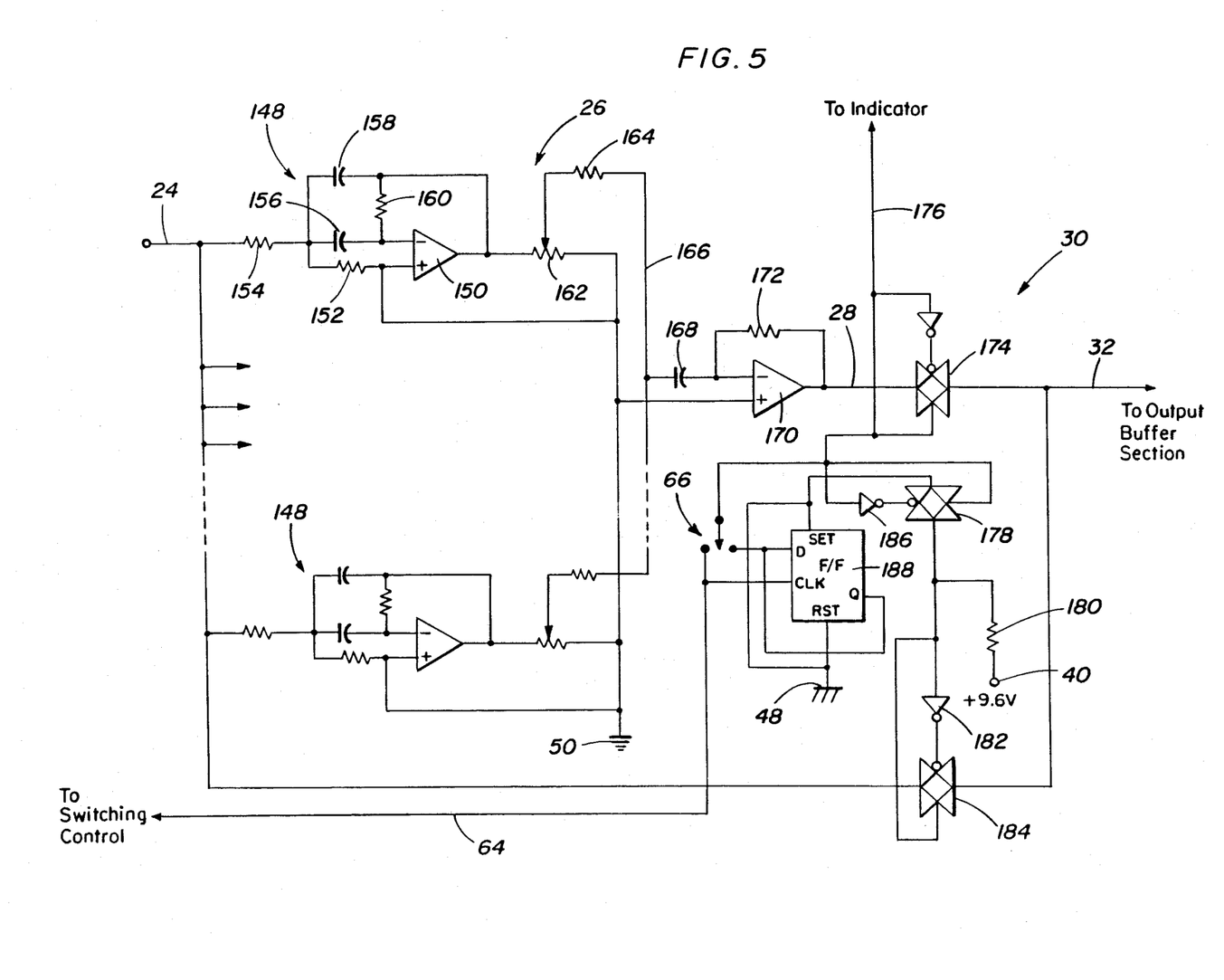

The amplified audio signal in line 24 is fed to ten identical bandpass amplifier circuits 148 interconnected in parallel to line 24 in the bandpass section 26, two of such amplifier circuits being shown in FIG. 5. Each amplifier circuit 148 includes an operational amplifier 150 having its non-inverting input terminal connected to line 24 through series connected resistors 152 and 154. Line 24 is coupled by resistor 154 and capacitor 156 to the inverting input terminal in parallel with capacitor 158 and feedback resistor 160 connected to the output terminal. The output terminal is also connected by adjustable resistor 162 and resistor 164 to a common signal output line 166. The Q factor for all amplifier circuits 148 is set at approximately 2.5 for example, while the resistance ratios of resistors 160 and 154 is selected to obtain the same pass-band amplification factor of −0.25, for example. Different bandpass center frequencies for the respective amplifier circuits 148 are obtained by proper selection of the capacitances of capacitors 156 and 158 while bandpass signal component amplitudes are adjusted through resistors 162.

All bandpass signal components passed by resistors 162 and 164 are fed by DC blocking capacitor 168 to the inverting input terminal of a operational amplifier 170 arranged in an inverting, audio summing configuration by connecting the non-inverting input terminal to ground 50 and interconnecting the inverting input and output terminals by feedback resistor 172. The output terminal line 28 from the summing amplifier 170 is connected by transmission gate 174 of the gate section 30 to the output buffer section 34 through line 32. Transmission gate 174 is turned on and off under control of the switching control section 44 through the bandpass select command line 64 when mode selector 66 is in a momentary bandpass mode position connecting command line 64 to gate 174 through line 176 to which the indicator section 54 is also connected. A command signal in line 64 produced by actuation of touch switch 62 will be directly transferred to gates 174 and 178 to turn them on and route the output signal from bandpass section 26 through gate 174 to line 32. In such case gate 178 is turned on and maintained on momentarily, provided power is supplied thereto at +9.6V through resistor 180. Resistor 180 is also connected through inverter 182 to transmission gate 184 causing it to turn-off at the same time. Gate 184 directly interconnects the line 24 with the output line 32 to establish a by-pass route. Thus, a turn-off signal in command line 64 is operative through inverters 186 and 188 to turn off the gates 178 and 184 to by-pass bandpass section 26 and enable gate 174 to be turned on and establish the by-pass route.

When the mode selector 66 is displaced to its other mode position, flip-flop 88 is toggled on and off by the select command signals in line 64. Flip-flop 188 is arranged in a divide by two configuration so as to toggle its Q output each time a positive going pulse is sensed at its D terminal, which is then connected by switch 66 to line 176 to which such pulses are transferred. Thus, each actuation of touch switch 62 alternatively switches in and switches out the bandpass section 26.

Figure 4:
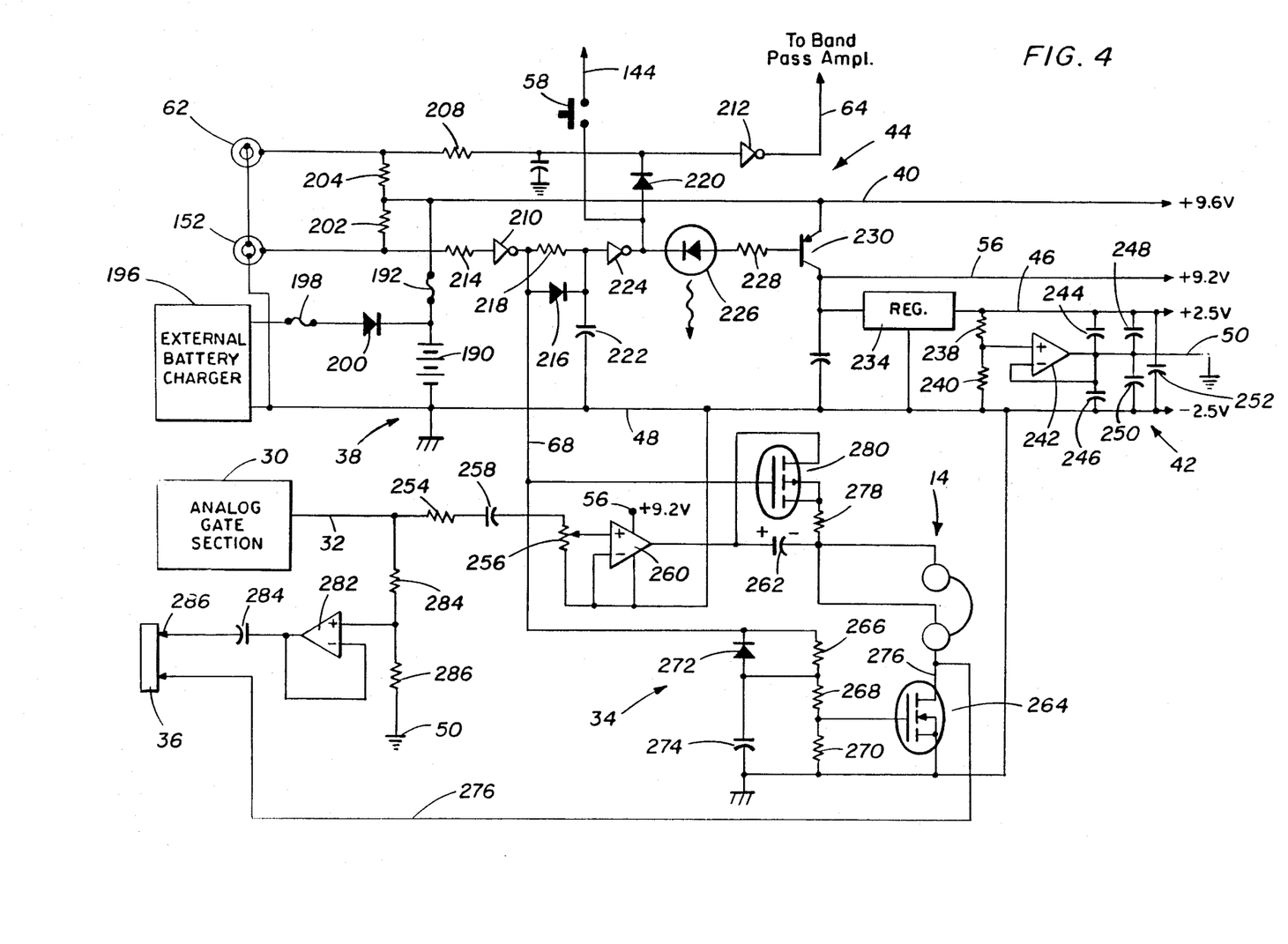

The power source 38 as shown in FIG. 4 includes a rechargeable battery 140 having a negative terminal connected to the digital ground 48 at −2.5 volts. The positive terminal of the battery is connected through a fuse 192 to power supply line 40 through which all digital components are continuously powered at a +9.6 volt level. The battery may be recharged from an external charger 196 connected to its negative terminal and through fuse 198 and rectifying diode 200 to the positive terminal. The positive terminal of the battery powers the switching control section 44 through line 40.

The power supply line 40 is connected through resistors 202 and 204 in the switching control section 44 to the touch switches 62 and 52, respectively, through which the signal commands are generated and respectively applied through current limiting resistors 206 and 208 to Schmitt inverters 210 and 212. The inverter 210 under control of the touch switch 52 feeds on/off power supply commands to the output buffer 34 through line 68 while the inverter 212 feeds bandpass select commands under control of touch switch 62 to the by-pass control gate section 30 through line 64.

When the ausculscope is off, power voltage line 40 applies the relatively high voltage (9.6VDC) through resistor 202 to the touch switch 52 and through current limiting resistor 214 to the inverter 210. A high voltage is then also applied through diode 216 to the output side of inverter 210 in series with resistor 218 connected in parallel with diode 216. A low is thereby maintained on the bandpass select line 64 connected to the output side of inverter 214 to prevent any toggling in the control gate section 30. Any negative-going pulses applied to line 64 by actuation of touch switch 62 will not ground inverter 212 at its input side because of current flow through diode 220 to disable the bandpass select operation. Also, diode 220 will then remove any negative reference from line 144 connected to AGC select switch 58 to disable its operation in exercizing toggle control over flip-flop 188 in the automatic gain control section 22 as aforementioned.

When the ausculscope is on, diode 220 is reverse biased to release its disabling action on operation of touch switch 62. Negative-going pulses generated by actuation of touch switch 62 will then be allowed to toggle the control gate section 30 through line 64.

The parallel connected resistor 218 and diode 216 aforementioned together with capacitor 222 connected to digital ground 48 form a modified low pass filter. When touch switch 52 is actuated, diode 216 short circuits resistor 218 to rapidly charge capacitor 222 toward the voltage level in line 40 to produce a power-on signal at the output of inverter 224. Upon release of touch switch 52, the output of inverter 210 goes low to reverse bias diode 218 so that capacitor 22 is slowly discharged through resistor 218 for delaying the power-off signal at the output of inverter 224.

The output side of inverter 224 is connected in series with LED indicator lamp 226 and resistor 228 to the input base of a transistor 230 having its collector connected to the power supply line 40. A power-on signal from inverter 224 switches on transistor 230 to supply operating voltage from line 40 through line 232 to the indicator section 54 and to the input terminal of a voltage regulator 234 in the power splitting section 42. The output terminal of regulator 234 supplies +2.5 voltage through line 56 to the audio amplifiers of sections 16 and 22 whenever the ausculscope is switched on.

The power fed from regulator 234 is split between line 56 (at +2.5V) and the negative digital ground line 48, aforementioned, by a power supply converter formed by voltage dividing resistors 238 and 240, operational amplifiere 242 and filter capacitors 244 and 246. Resistors 230 and 240 are interconnected in series between line 236 and ground 48, and their junction is connected to the non-inverting input terminal of amplifier 242, the inverting terminal of which is connected to the junction between the output terminal and the filter capacitors 244 and 246, respectively connected to lines 263 and ground 48. The output junction of amplifier 242 itself is connected to ground 50. The amplifier 242 is thus arranged in a unity gain, voltage follower configuration to maintain a 2.5VDC charge across the capacitors 244 and 246. Additional high frequency filtering for the power supply is provided for by the capacitors 248, 250 and 252. Split power supply between ground 48 and line 46 is thereby satisfied to meet the requirements of the bandpass section 26 and the automatic gain control section 22 as hereinbefore described.

The analog output signal from the gate section 30 is attenuated by resistor 254 in conjunction with an adjustable volume control resistor 256 interconnected in series by DC blocking capacitor 258 between line 32 and the non-inverting input terminal of a low voltage audio power amplifier 260 in the buffer section 34. The capacitor 258 provides conversion from the analog ground 50, with respect to which the analog signal is referenced and the digital ground 48 with respect to which the output of amplifier 260 is referenced. The output of amplifier 260 is coupled through capacitor 262 to the speaker/headphones 14. Capacitor 262 completes the reference level shift to digital ground.

In order to permit settling of the power supplies and signal processing circuitry when operation of the ausculscope is initiated, the headphones 14 are momentarily disconnected under control of a MOS field effect transistor 264 acting as a switch. The input gate of transistor 264 is therefore connected to control line 68 from the switching control section 44 through a delay network formed by a resistive branch having resistors 266, 268 and 270 connected in series between control line 68 and digital ground 48. A diode 272 is connected across resistor 266 and a capacitor 274 is connected across the resistors 268 and 270. The junction between the resistors 268 and 270 is connected to the input gate of transistor 264.

While the ausculscope is off, control line 68 is low to hold capacitor 274 fully discharged through resistor 266 and diode 274. A cut-off voltage will then be held on the gate of transistor 264 so as to allow ground lead 276 of the headphones 14 to float. When power is applied to control line 68, capacitor 274 is slowly charged through resistor 266 until it reaches a level applying a switch-on voltage through resistor 268 to the gate of transistor 264. The capacitor 274 continues to charge causing the gate voltage level to the further rise until full saturation is reached. Such slow turn on of transistor 264 causes the negative side of capacitor 262 to discharge slowly through the headphones so as to minimize noise as the transistor 264 approaches full saturation and applies the full negative voltage level of ground 48 to the ground lead 270 of the headphones, connected to the output drain of transistor 264. When power is turned off again, control line 68 goes low so that capacitor 274 rapidly discharges through diode 272 and cause the gate voltage of the transistor 264 to go to zero for rapid turn off. The headphones are thereby rapidly disconnected from ground 48 to prevent transients and noises being reproduced in the headphones during the sequence initiated by a power down command signal in control line 68 from the switching control section 44 as hereinbefore described.

Before the power down sequence is completed, capacitor 262 is discharged through resistor 278 and the source-drain circuit of field effect transistor 280 to prevent "pop" noise in the headphones. Transistor 280 accordingly has its source-drain circuit connected in series with resistor 278 across the capacitor 262, and its input gate connected to control line 68.

A high impedance output buffer to the stereo phono jack 36 as compared to the low impedance buffer to speakers 14 is formed by an amplifier 282 having its non-inverting input terminal connected to the junction between resistors 284 and 286, respectively connected to the analog signal line 32 and the analog reference ground 50. The output terminal of amplifier 282 has a feedback connection to its inverting input terminal to establish a simple voltage follower operation isolating the output signal coupled by a DC blocking capacitor 284 to the tip terminal 286 of the jack 36, which has a ring terminal 288 to which the headphone ground lead 276 is connected.

As shown in FIG. 3, the indicator section 54 includes a pair of LED indicator lamps 290 and 292. LED lamp 290 is connected by diode 294, resistor 296 and inverter 298, the $\overline{Q}$ output of flip-flop 134 associated with the negative feedback loop portion of the AGC section 22. The LED lamp 292 is connected by diode 300, resistor 302, inverter 304 and line 176 to the digital gate circuitry of the gate section 30. Thus, both LED lamps will be illuminated when the $\overline{Q}$ output of flip-flop 134 is high and gate 174 is off in the AGC section 22 and gate 30, respectively, signifying fixed gain operation and bandpass by-pass, provided power is being supplied to the indcator lamps through the +9.2V volt line 56 in response to a power select command. Both lamps 290 and 292 are accordingly connected in parallel to line 56 as shown in FIG. 3. The indicator lamps will be extinguished, on the other hand, during normal automatic gain and bandpass operation of the ausculscope.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. In an electronic ausculscope having a pick-up transducer, a preamplifier to the transducer, automatic gain control means connected to the preamplifier for variable amplification of audio signals transmitted from the transducer, speaker means for reproducing the audio signals amplified by the automatic gain control means, output buffer means operatively by connected to the automatic gain control means for driving the speaker means and bandpass means connected to the automatic gain control means for limiting transmission of the amplified audio signals to selected bandpass frequencies, the improvement comprising selectively controlled supply means for powering the preamplifier and the output buffer means in response to command signals and selectively controlled gate means connected to the output buffer means and the automatic gain control means for by-pass of the bandpass means.

2. The improvement as defined in claim 1 wherein said power supply means includes a power continuously powering the automatic gain control means and the gate means at a relatively high voltage, switching control means continuously powered by the source at said high voltage for generating said command signals, power splitting means connected to the source for powering the preamplifier at a relatively low voltage in response to said command signals and selective switch means connected to the switching control means for initiating said generation of the command signals and controlling operation of the gate means.

3. The improvement as defined in claim 2 including selectively operated means for disabling operation of the automatic gain control means as a variable gain amplifier.

4. The improvement as defined in claim 3 including grounding means connected to the power splitting means for maintaining a constant reference level for the high and low voltages supplied by the power source and the switching control means, said constant reference level being equal and opposite in polarity to the relatively low voltage.

5. The improvement as defined in claim 4 wherein the output buffer means includes an output amplifier powered in response to the command signals and ground establishing circuit means connected to the grounding means in series with the output amplifier and the speaker means in delayed response to the command signals.

6. The improvement as defined in claim 5 including indicator means powered simultaneously with the output amplifier of the buffer means and connected to the automatic gain control means and the gate means for indicating the operational thereof.

7. The improvement as defined in claim 6 including mode selector means connected to the gate means for by-passing the bandpass means either by each actuation of the selective switch means or alternate actuation of the selective switch means.

8. The improvement as defined by claim 7 wherein the selective switch means includes a power select switch and a bandpass select switch, said switching control means having separate circuit portions respectively connecting the power and bandpass select switches to the power splitting means and the gate means.

9. The improvement as defined by claim 8 wherein the disabling means is connected to that circuit portion of the switch control means to which the power splitting means is connected.

10. The improvement as defined in claim 9 wherein the automatic gain control means includes an operational amplifier interconnecting the preamplifier and the bandpass means and feedlock loop means connected to the operational amplifier for varying signal gain therethrough as an inverse function of input signal amplitude below a predetermined amplitude limit.

11. The improvement as defined in claim 1 including selectively operated means for disabling operation of the automatic gain control means as a variable gain amplifier.

12. The improvement as defined in claim 11 wherein the automatic gain control means includes an operational amplifier interconnecting the preamplifier and the bandpass means and feedback loop means connected to the operational amplifier for varying signal gain therethrough as an inverse function of input signal amplitude below a predetermined amplitude limit.

13. The improvement as defined in claim 2 including grounding means connected to the power splitting means for maintaining a constant reference level for the high and low voltages supplied by the power source and the switching control means, said constant reference level being equal and opposite in polarity to the relatively low voltage.

14. The improvement as defined in claim 13 wherein the output buffer means includes an output amplifier powered in response to the command signals and ground establishing circuit means connected to the grounding means in series with the output amplifier and the speaker means in delayed response to the command signals.

15. The improvement as defined in claim 14 including indicator means powered simultaneously with the output amplifier of the buffer means and connected to the automatic gain control means and the gate means for indicating the operational conditions thereof.

16. The improvment as defined in claim 2 including mode selector means connected to the gate means for by-passing the bandpass means either by each actuation of the selective switch means or alternate actuation of the selective switch means.

17. The improvement as defined in claim 2 wherein the selective switch means includes a power select switch and a bandpass select switch, said switching control means including separate circuit portions respectively connecting the power and bandpass select switches to the power splitting means and the gate means.

18. The improvement as defined in claim 17 including selectively operated means for disabling operation of the automatic gain control means as a variable gain amplifier.

19. The improvement as defined in claim 18 wherein the selectively operated disabling means is connected to that circuit portion of the switching control means to which the power splitting means is connected.

20. In an electronic ausculscope having a pick-up transducer, an output speaker and bandpass means operatively interconnecting the transducer and the speaker for transmission of audio signals to the speaker, the improvement comprising selectively controlled power supply means for powering the ausculscope in response to command signals and gate means connected to the bandpass means for selective by-pass thereof during processing of the audio signals transmitted between the transducer and the speaker, said bandpass means including a plurality of filters having different predetermined bandpass frequencies and a common predetermined Q factor.

21. In an electronic ausculscope having a pick-up transducer, an output and bandpass amplifier means operatively interconnecting the transducer and the speaker for limiting transmission of audio signals to selected bandpass frequencies, the improvement comprising selectively controlled power supply means for powering the ausculscope in response to command signals and gate means connected to bandpass amplifier means for selective by-pass thereof during processing of the audio signals transmitted between the transducer and the speaker, said power supply means including a power source continuously powering the gate means, switching control means continuously powered by the source for generating said command signals and signal conducting means connecting the switching control means to the gate means for by-passing the bandpass amplifier means in response to said command signals.

22. In an electronic ausculscope having a pick-up transducer, an output speaker and amplifier means for transmitting audio signals from the transducer to the speaker, the improvement comprising a power source continuously powering the amplifier means at a predetermined operating voltage, switching control means continuously powered by the source for generating command signals, powered splitting means responsive to said command signals for estabishing a reference ground level, loop means operatively connected to said amplifier means in response to the establishment of said reference ground level for varying signal gain as an inverse function of input signal amplitude below a predetermined amplitude limit and selectively operated means for transmitting the command signals to the feedback loop means to enable operation thereof.

23. In a signal processing device having an input, an output, analog circuit means operatively interconnecting the input and output for processing signals transmitted therebetween and selectively controlled digital circuit means producing command signals for controlling operation of the analog circuit means, the improvement comprising power means connected to the digital circuit means for continuous energization thereof at an operating voltage and switch controlled supply means continuously energized by the power means for energization of the analog circuit means in response to the command signals, said analog circuit means including an audio amplifier and a bandpass circuit, said input comprising a microphone connected to the amplifier and said output comprising a speaker and an output buffer connecting the bandpass circuit to the speaker.

24. The improvement as defined in claim 23 including ground means connected to the digital circuit means and means operated by the switch controlled supply means for generating a reference voltage level applied to the ground means of a polarity opposite to said operating voltage.

25. The improvement as defined in claim 24 wherein the digital circuit means includes signal gate means for selectively connecting the audio amplifier to the output buffer in by-pass relation to the bandpass circuit, feedback loop means connected to the audio amplifier for varying signal gain therethrough as an inverse function of input signal amplitude below a predetermined amplitude limit, a pair of select signal switches, and means connected to said switches for generating said command signals.

26. The improvement as defined in claim 23 wherein the digital circuit means includes signal gate means for selectively connecting the audio amplifier to the output buffer in by-pass relation to the bandpass circuit, feedback loop means connected to the audio amplifier for varying signal gain therethrough as an inverse function of input signal amplitude below a predetermined amplitude limit, a pair of select signal switches, and means connected to said switches for generating said command signals.

27. In an electronic ausculscope having a microphone, output speaker means for audio reproduction of sounds picked up by the microphone and bandpass means operatively interconnected between the microphone and the speaker means for selectively processing the sounds picked up prior to said audio reproduction thereof, including a plurality of filters having different predetermined bandpass frequencies and a predetermined Q factor.

* * * * *